United States Patent [19]

Fallone et al.

[11] Patent Number: 5,686,733

[45] Date of Patent: Nov. 11, 1997

[54] MEGAVOLTAGE IMAGING METHOD USING A COMBINATION OF A PHOTORECEPTOR WITH A HIGH ENERGY PHOTON CONVERTER AND INTENSIFIER

[75] Inventors: Biagio Gino Fallone, Montréal-Nord; Tony Falco, Montréal, both of Canada

[73] Assignee: McGill University, Montreal, Canada

[21] Appl. No.: 625,063

[22] Filed: Mar. 29, 1996

[51] Int. Cl.⁶ .................................................. G01T 1/24
[52] U.S. Cl. .................. 250/591; 250/580; 250/370.09; 250/370.12
[58] Field of Search .................................. 250/591, 580, 250/370.12, 370.11, 370.09

[56] References Cited

U.S. PATENT DOCUMENTS

| | | | |
|---|---|---|---|
| 4,249,106 | 2/1981 | Maruyama et al. | 313/365 |
| 4,577,108 | 3/1986 | Diepers et al. | 250/370.09 |
| 4,770,965 | 9/1988 | Fender et al. | 430/66 |
| 4,823,370 | 4/1989 | Kikuchi | 378/99 |
| 4,920,012 | 4/1990 | Woodruff et al. | 428/634 |
| 4,961,209 | 10/1990 | Rowlands et al. | 378/29 |
| 4,969,176 | 11/1990 | Marinus | 378/149 |
| 5,262,649 | 11/1993 | Antonuk et al. | 250/370.09 |
| 5,300,784 | 4/1994 | Fender et al. | 250/484.2 |
| 5,320,927 | 6/1994 | Fender et al. | 430/128 |

FOREIGN PATENT DOCUMENTS

| | | |
|---|---|---|
| 0 548 407 | 6/1993 | European Pat. Off. |
| 0 565 766 | 10/1993 | European Pat. Off. |
| 60-190884 | 9/1985 | Japan ................ 250/580 |

OTHER PUBLICATIONS

Naruse et al., "Metal/Amorphous Silicon Multilayer Radiation Detectors." IEEE Transactions on Nuclear Science, 1989, 36(2), 1347–1352.

Wowk et al., "Thick Phosphor Screens for On–line Portal Imaging." Med. Phys., 1994, 21(8), 1269–1274.

Dong et al., "An Objective Method for Evaluating Electronic Portal Imaging Devices." Med. Phys., 1994, 21(6), 755–760.

Wowk et al., "Grooved Phosphor Screens for On–line Portal Imaging." Med. Phys., 1993, 20(6), 1641–1651.

Antonuk et al., "Demonstration of Megavoltage and Diagnostic X–Ray Imaging with Hydrogenated Amorphous Silicon Arrays." Med. Phys., 1992, 19(6), 1467–1473.

Boone, "Parametrized X–ray Absorption in Diagnostic Radiology from Monte Carlo Calculations: Implications for X–ray Detector Design." Med. Phys., 1992, 19(6), 1455–1458.

Boyer et al., "Review of Electronic Portal Imaging Devices (EPIDS)." Med. Phys., 1992, 19(1), 1–16.

Barnea et al., "Use of Storage Phosphor Imaging Plates in Portal Imaging and High–energy Radiography: The Intensifying Effect of Metallic Screens on the Sensitivity." Med. Phys., 1991, 18(3), 432–438.

(List continued on next page.)

*Primary Examiner*—Constantine Hannaher
*Attorney, Agent, or Firm*—Fitzpatrick, Cella, Harper & Scinto

[57] ABSTRACT

Megavoltage imaging method and apparatus are provided to monitor a target volume of a patient in real time. Structure and steps are provided for generating an image on a detector (having a layer of photoreceptor material deposited on a layer of a high density substrate) by passing a photon beam first through the target volume of the patient and subsequently through the detector. The layer of the high density substrate is on the side of incidence of the photon beam for intensifying photon quanta and filter-scattered radiation from the patient induced by the photon beam. Thus, the photons impinging on the high density substrate are converted to electrons, and the images generated by the electrons subsequently traversing the photoreceptor material to cause the target volume of the patient to be monitored in real time.

18 Claims, 6 Drawing Sheets

OTHER PUBLICATIONS

Droege et al., "Influence of Metal Screens on Contrast in Megavoltage X-ray Imaging." Med. Phys., 1979, 6(6), 487–493.

Shalev, "Progress in the Evaluation of Electronic Portal Imaging–Taking One Step at a Time." Int. J. Radiation Oncology Biol. Phys., 1994, 28(4), 1043–1045.

Zanella et al., "The Detective Quantum Efficiency of an Imaging Detector." Nuclear Instruments and Methods in Physics Research, 1995, A 359, 474–477.

Mosleh–Shirazi et al., "Monte Carlo Simulations of CsI(Tl) Scintillation Crystals for Use in a Three–Dimensional Megavoltage CT Scanner." Nuclear Instruments and Methods in Physics Research, 1994, A 348, 563–566.

Fig. 6A
Fig. 6B
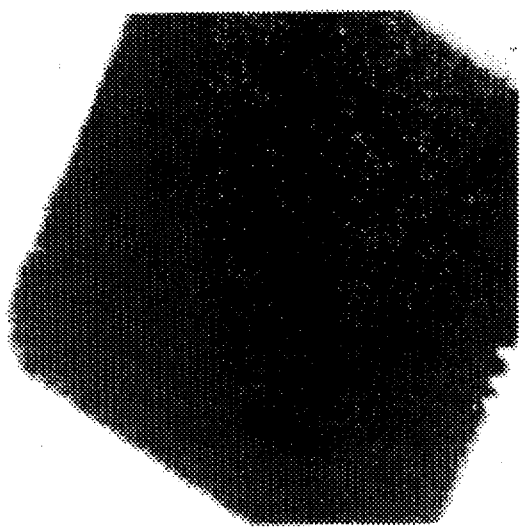
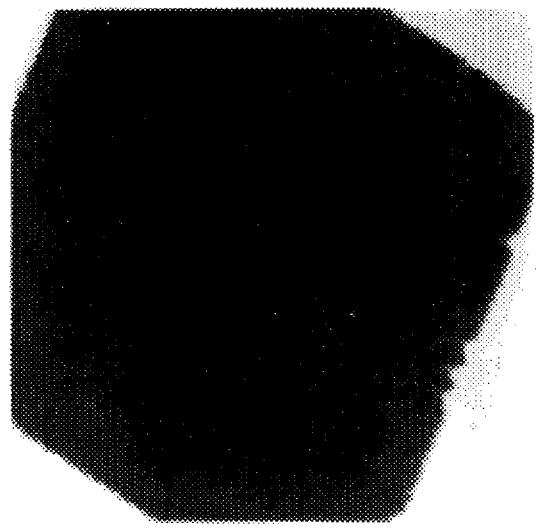
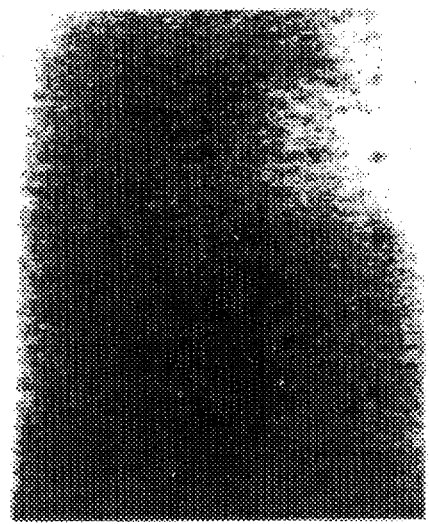
Fig. 7A
Fig. 7B

MEGAVOLTAGE IMAGING METHOD USING A COMBINATION OF A PHOTORECEPTOR WITH A HIGH ENERGY PHOTON CONVERTER AND INTENSIFIER

FIELD OF THE INVENTION

The present invention is concerned with a novel imaging method for obtaining images of better quality in real time in the field of megavoltage imaging. The invention also comprises a novel detector to be used in association with the novel imaging method.

BACKGROUND OF THE INVENTION

In conventional xeroradiographic methods, the image is formed by the x-rays directly absorbed within an amorphous selenium (a-Se) layer. For low energy x-ray photons used in diagnostic radiology, this results in acceptable radiographic images. However, in radiation oncology, most of the high energy photons, typically from about 0.5 MeV to about 25 MeV, would traverse the a-Se medium without being absorbed, thus decreasing the quantum detective efficiency. Furthermore, the high energy beam, or megavoltage beam, would produce a large amount of scattered radiation within the patient which in ram, would disperse onto the a-Se layer resulting in a very blurred image.

When external beam radiation therapy is used to control and annihilate a tumorous mass, extreme care must be taken to irradiate the anatomical region prescribed for treatment while limiting the amount of energy received, through radiation, by the surrounding healthy tissue. This implies that localization errors must be minimized when placing the treatment field over the intended treatment volume to avoid complications. Imaging with a high energy beam prior to the treatment, which is known in the art equally well as megavoltage imaging, therapy imaging or portal imaging, is used as a method to monitor the treatment beam field position vis-a-vis the target volume. It is referred to as portal imaging because the image of the anatomy is obtained through the collimated opening, or port, of the therapy machine. This type of imaging was made possible some twenty years ago, with the advent of slower film emulsions, or portal films, tailored for high energy images. Several authors have shown that an increase in the use of portal imaging has decreased the frequency of localization errors, which implies better tumor control. It has been reported that a 5-mm reduction in placement errors could result in 10–20% improvement in tumor control.

Portal films are placed between metal detectors and/or fluorescent screens to increase the so-called intensification factor, which is the number of electrons and photons generating the image on the film. Unfortunately, there are several drawbacks to the use of portal films for setup quality assurance:

portal images offer very low image contrast due largely to the low subject contrast that is inherent to high energy beams and due to the saturation characteristics of the film beyond a certain dose;

it is a very time-consuming process for the radiation oncologist to find recognizable details in portal images which are then matched to the initially delineated prescription field of simulation radiographs obtained at diagnostic energies; and because of delays encountered in the development of the portal radiographs, the portal films are very rarely taken for each treatment setup. In general, portal images are taken only once or twice during the whole treatment which usually consists of several fractions or separate treatment sessions. Often, several treatment sessions are done before portal films are taken.

Conventional xeroradiographic detectors have been used experimentally for therapy images with limited success. Delays in the electrostatic powder development, insufficient sensitivity of the system with high energy therapy photons and increased patient scatter has seriously limited its use in portal imaging.

Digital electronic portal imaging devices (EPIDs) have addressed the problem of extracting as much information from the low inherent subject contrast of therapy energies, as well as to eliminate the time delay problems involved with the chemical development of portal radiographs. Experimental and commercial EPIDs involve the following technologies: fluoroscopic imaging techniques, liquid ionization chambers or linear diode arrays. Fluoroscopic imaging detectors use scintillating materials such as phosphor to convert the radiation energy (photons+electrons) into optical photons. These optical photons are then guided through an optical system (mirror+lens) and detected by photo sensitive materials like video cameras or charge-coupled devices (CCD). However, due to the poor quantum efficiency of such detectors, mainly because of the optical system, the image quality is necessarily low and many frames must be averaged to produce acceptable images. The detector is also bulky because of the use of folding mirror optics. Another technology uses a liquid to convert the radiation energy (photons+electrons) to charges (electrons+ions). An electric field is applied and the moving charges produce a current which is collected in a plurality of electrometers. Because of the low x-ray absorption of the liquid, compared to phosphor, the system sensitivity is rather low, thus requiting higher dose to create an acceptable image. (see *Med. Phys.*, 1994, 21(6), 755–760).

The on-line characteristics of the above devices and the fact that the images can be obtained in real time makes them very appealing. Nevertheless, portal radiographs (metal detector-film combinations) are still the most commonly used form of geometric setup control practiced in radiotherapy centers, mostly because of their superior imaging quality as compared to contemporary EPIDS.

In U.S. Pat. No. 4,961,209, an x-ray image-scanning system is disclosed which uses a conventional flat selenium photoreceptor having a movable transparent slit sensor electrode through which a traversing light beam discharges the photoreceptor in a raster pattern after x-ray exposure.

In U.S. Pat. No. 4,770,965, an electrophotographic imaging member comprising a conductive substrate, an alloy layer made of selenium doped with arsenic is described. The substrate may be an opaque metal such as aluminum combined with an electrically conductive material like aluminum, titanium, nickel, chromium, brass, copper, zinc, silver, tin etc.

In U.S. Pat. No. 5,320,927, there is provided a method of vacuum depositing a selenium-arsenic coating on a substrate to form a photoreceptor. The patent also discloses a detector for electrophotographic imaging comprising the selenium-arsenic alloy and either a tin-oxide coated substrate or an aluminum substrate.

In U.S. Pat. No. 5,300,784, a selenium alloy electrophotographic imaging member having an optically transparent glass and tin oxide coated substrate is described. The x-ray image is formed on the side of the photoreceptor, and is scanned through the transparent substrate with a fine beam of light.

In EP 0 565 766, a technique is discussed for coating a substrate with a copper film. Although the substrates referred to in the specification are plastic and/or organic, it is also mentioned that the method could be effectively used with other substrates. Yet, no direct mention of a selenium substrate was made, and furthermore no imaging use at megavoltage energies is proposed for these substrates.

Another system is also depicted in IEEE *Trans. Nuclear Science*, 1989, 36, 1347–1352. The system is a radiation detector following the principle of increased sensitivity with high Z material However, no spatial information is provided, and therefore this cannot be considered a 2D imaging sensor.

In U.S. Pat. No. 5,262,649, a thin film pixelated detector array is described using a metal plate, a phosphor and an array of photosensitive sensors of hydrogenated amorphous silicon. Although it is mentioned that it may be possible to increase the thickness of the sensors so that a metal plate and phosphor layer would become unnecessary, this has not been verified in the patent. In other words, a phosphor layer is required to convert radiation to light, which is subsequently captured by the amorphous silicon layer and converted to spatial information.

There still remains a need to improve imaging systems for portal imaging. Improved imaging quality could be obtained by using an intensifier of quanta information. None of the above references mention, disclose or suggest a metal substrate, or other material, as an intensifier of quanta information, nor a method of shielding the low energy sensitive photoreceptor material from the impinging patient scatter in portal imaging.

SUMMARY OF THE INVENTION

In accordance with the present invention, there is now provided an improved imaging method to monitor in real time the treatment beam field position vis-a-vis the target volume of a patient. More specifically, the method comprises placing the photon converting substrate of the detector on the side of incidence of the high energy x-ray beam with the photoreceptor material sensitive to radiation being on the opposite side, the substrate being made of a high physical density material, preferably a conductor. In operation, the photons impinge on the high physical density material and are converted to electrons. The image is subsequently generated on the photoreceptor material by the electrons traversing therethrough.

The present application is also concerned with a novel detector comprising a substrate made of high physical density material, preferably a conductive material, with a layer of a photoreceptor material deposited thereon. Preferred photoreceptor materials include amorphous selenium, mercuric iodide, cadmium telluride, lead oxide and the like.

IN THE DRAWINGS

Figure 8:
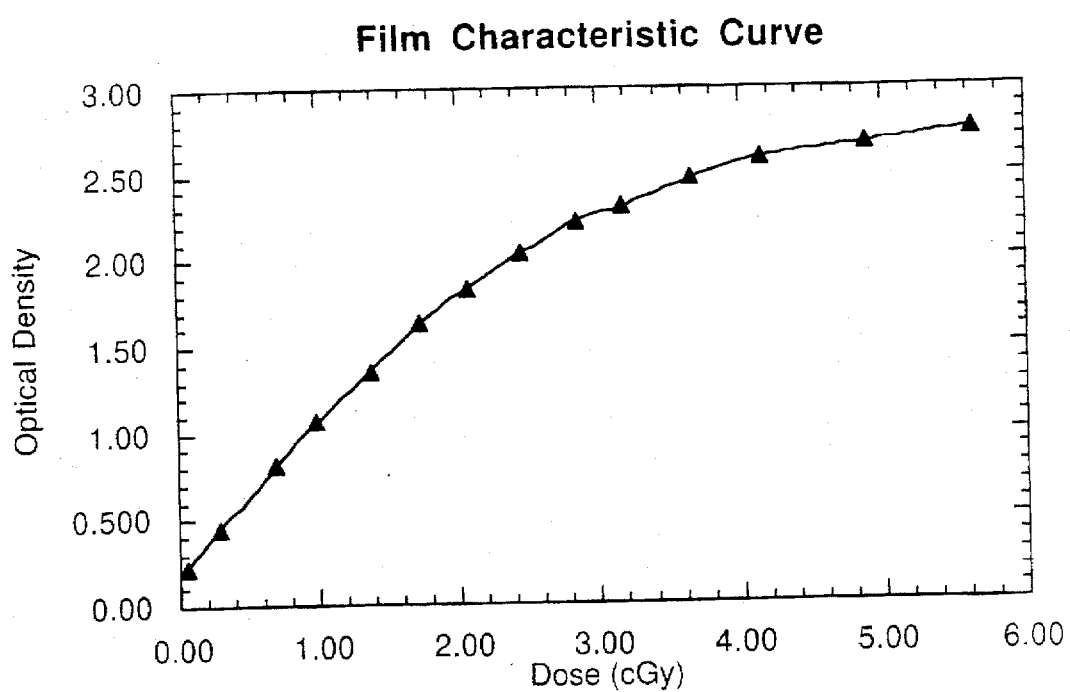

FIG. 6a and 6b illustrates contrast-detailed phantom images from a Co-60 therapy machine, with the 1 mm copper substrate and 300 micron a-Se detector for both the substrate facing towards (6a) and away from the source (6b);

FIG. 7a and 7b illustrates contrast-detailed phantom images for the 1 mm thick copper substrate (300 micron thick a-Se layer) detector with the substrate facing towards (7a) and away (7b) from the source as obtained from a Clinac-2300 C/D therapy machine. All the images were obtained with irradiations of 0.6 cGy at the imaging plane; and FIG. 8 illustrates the film characteristic curve for the RP Kodak therapy localization film obtained from the Clinac-18 10 MV photon beam and from the Cobalt-60 machine.

DETAILED DESCRIPTION OF THE INVENTION

The present invention is concerned with an imaging method providing radiation oncology therapy images of significantly better quality, and used for localization prior to treatment, and for verification of the treatment of cancer lesions. The proposed method differs in two ways from conventional xeroradiographic methods. First, the x-ray beam enters the detector on the substrate side, the photoreceptor material layer being on the opposite side. Secondly, the substrate of the detector is composed of a high physical density material layer, preferably a conductor, rather than the low physical density and passive aluminum metal layer used conventionally in xeroradiography. The electrostatic latent image may then be read conventionally, for example, by scanning with an electrostatic non-contact probe or probe array, a photoinduced discharge scanning laser beam method in conjunction with an active matrix self-scanning system, a self-scan voltage switching system, a projection system, and the like.

A brief description of various readout methods that can be used follows.

1. Non-contact voltage or charge probe or probe array: A non-contact probe or linear probe array that measures either voltage or charge or current is used to scan either in raster fashion or linear fashion across the 2-dimensional surface of the detector, or a 2D probe array that measures either voltage or charge on the surface of the detector without any lateral or longitudinal motion.

2. Photoinduced discharge scanning laser beam method The readout approach is based on a scanning blue-laser beam to cause photoinduced discharge in the solid-state duodielectric structure.

3. Active matrix self-scanning system A detector with a photoreceptor layer to convert incident x-rays to electron- hole pairs, which are then separated and drawn to the surface of the photoreceptor material by an applied electric field. The resultant charge latent image is read in situ with a large area active matrix array of cadmium selenide thin film transistors or of hydrogenated amorphous silicon arrays of thin film transistors and photodiodes.

4. Self-scan voltage switching systems The approach is based on arrays of switches, solid state or mechanical, and self-scanned charge/current detection. This implies the construction of two circuit boards each having thin parallel conductive strips, that "sandwich" the photoreceptor between them. Vacuum can be used to create good contact. The strips on the two circuit boards are perpendicular to each other with the strips on one board being connected to measuring or signal electrometers. Readings can be done during irradiation; the other board has strips that are perpendicular to measuring electrodes, each connected to a voltage switch. Each voltage electrode is subsequently activated and the resultant currents induced by the conversion of energy into electron-hole pairs are measured with the electrodes. Readings can also be done right after the irradiation. A polymer insulator is placed between the photoreceptor and the measuring strip electrodes. All of the voltage electrodes are connected to the required high voltage prior to irradiation to induce a polarization of charges at the surface of the photoreceptor. The external high voltage is removed, but the polarization across the photoreceptor will persist to separate the electron-hole pairs produced in the photoreceptor during the irradiation, and to draw them to the surface of the photoreceptor. Readout of the electrostatic latent image created at the interface of the photoreceptor and the polymer is performed by sequentially activating each voltage electrode to opposite polarity and having the resultant induced current measured with the measuring electrodes.

5. Reconstruction by filtered backprojection The high density conductive substrate is at high voltage during irradiation. Measuring strip electrodes are on a circuit board and placed on the other side of the photoreceptor. Each strip is connected to an electrometer. During irradiation the detector is mechanically rotated, and the resultant current from each strip electrode is measured. The curve of current versus time for each strip represents a projection similar to projections obtained in modern computed tomographic system. Using standard projection reconstruction techniques (e.g., filtered back projection, iterative, etc.) the current per 2-Dimensional pixel location is calculated.

Figure 2:
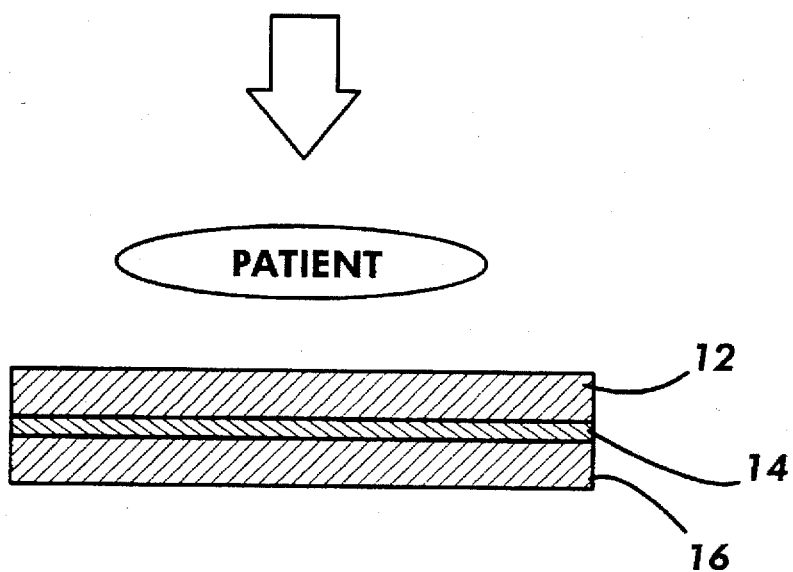
FIG. 2 illustrates a setup during treatment localization and/or verification using the a-Se detector with the metal substrate towards the source.

The detector has a high density substrate, preferably a conductive metal or alloy, placed at the entrance side of the beam towards the patient. In this manner, as illustrated in FIG. 2, the substrate acts as a medium gathering the x-ray or photon information. The substrate, which has a higher density, will absorb the high energy photons or x-rays impinging on it to a larger degree than the photoreceptor layer. The latent image is being formed on the photoreceptor material layer mainly by the electrons which are generated by the interaction of the patient-modulated photon beam with the substrate. The resultant electrons are preferentially scattered in the forward direction to subsequently interact with the photoreceptor material. Due to the charged nature of electrons, they will interact more readily within the photoreceptor layer than their photon counterpart. These interactions intensify the quanta of information reaching the photoreceptor material resulting in improved image quality at reasonable dosage. Thus, an image generated mainly by electrons traversing the photoreceptor material medium is obtained, as opposed to the photon generated images of conventional xeroradiography. The intensification effect due to the positioning of the substrate towards as opposed to away from the source can be seen in FIG. 4, wherein the exemplified substrate is copper.

Figure 5:
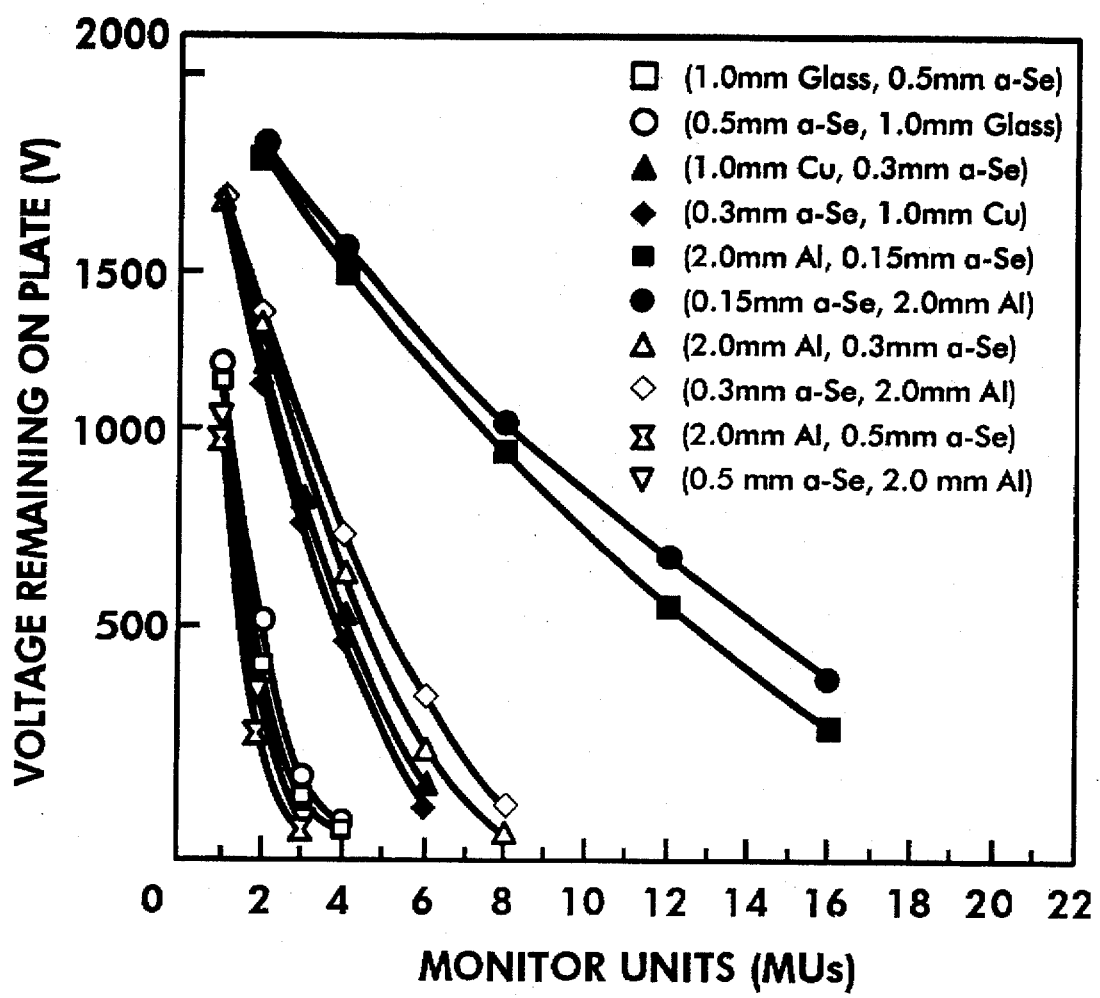
FIG. 5 illustrates various radiative-discharge (sensitivity) curves obtained from a Clinac-23 C/D (6 MV mode) therapy machine with three different substrates.

FIG. 5 illustrates the highly sensitive nature of a detector, wherein the photoreceptor material is amorphous selenium, to the low energy photons that exist in the spectrum of the Clinac-2300 CAD (6 MV mode) apparatus, but that does not exist in the spectrum of the Cobalt-60 unit. By placing the substrate towards the high energy photon source, the photoreceptor is shielded from the unwanted contaminating scattered electrons generated from the exiting layer of the patient, and to a smaller extent, the scattered lower energy photons generated by the patient. In this manner, the present detector can be considered (1) an intensifier of photon x-ray quanta, and (2) a filter of scattered radiation. Three substrates are illustrated: aluminum (thickness of 2 mm), glass-ITO (thickness of 1 mm), and copper (thickness of 1 mm) facing or away from the x-ray source. What is written first in the parenthesis in the legend of each graph indicates what is placed facing the source. Also compared is the different behavior between varying thicknesses of the photoreceptor layer (a-Se): the aluminum substrate with photoreceptor thicknesses of 150, 300, and 500 microns, the glass-ITO substrate with a 500 microns thick a-Se layer and the copper substrate with a 300 microns thick a-Se layer. As seen in the Figure, the thickness of the a-Se layer appears to control the range of information.

FIG. 6a and 6b illustrate results from imaging with a monoenergetic Co-60 beam. When imaging the contrast-detail phantom (each ~3cGy), it generates electron scatter and some lower energy photon scatter which simulate patient scatter. With the copper substrate facing the gamma ray source (FIG. 6a), a large portion of this scatter is removed and the phantom image can be obtained. On the other hand, when the copper substrate is away from the source (FIG. 6b), the image obtained contains the contribution from the phantom scatter and the details of the phantom image are destroyed. This fact is also evident for the images obtained from the Clinac-2300 C/D linear accelerator polyenergetic beam, as illustrated in FIG. 7a and 7b.

Any metal or alloy substrate is suitable for the purpose of removing the unwanted patient scatter, as long as the substrate thickness is equal to or larger than the average range of electrons for the given photon beam energy and detector type. The average electron range increases with an increase in photon beam energy. The required thickness of the front detector increases with a decrease in physical density thereof. Preferred substrates include aluminum, copper, iridium, brass, steel, iron, leaded glass, indium-tin-oxide (ITO) on glass (silicate), lead, tungsten and alloys thereof as functions of thicknesses. Copper, tungsten and stainless steel are most preferred for image resolution and quanta intensification, mainly because the range of the electrons and the resultant lateral scatter of the electrons generated in the substrate is shortened with increased density of the metal. This causes a more local deposition of energy within the photoreceptor material layer resulting in improved resolution. Furthermore, the number of Compton interactions per unit volume is greater for higher density metals or alloys, thus generating a larger electron flux.

Figure 1:
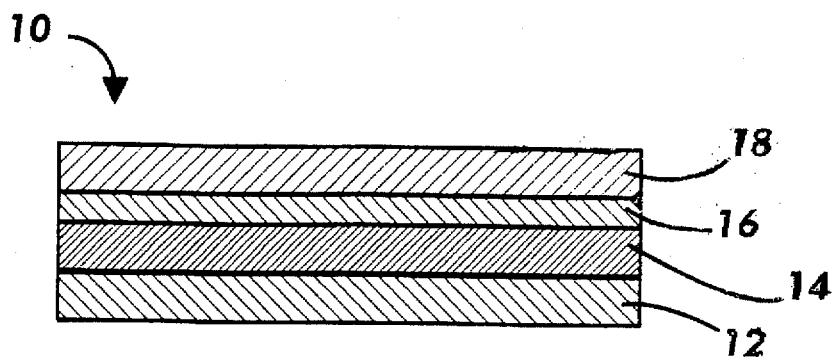
FIG. 1 is a cross-sectional view of the detector according to the present invention.
Figure 4:
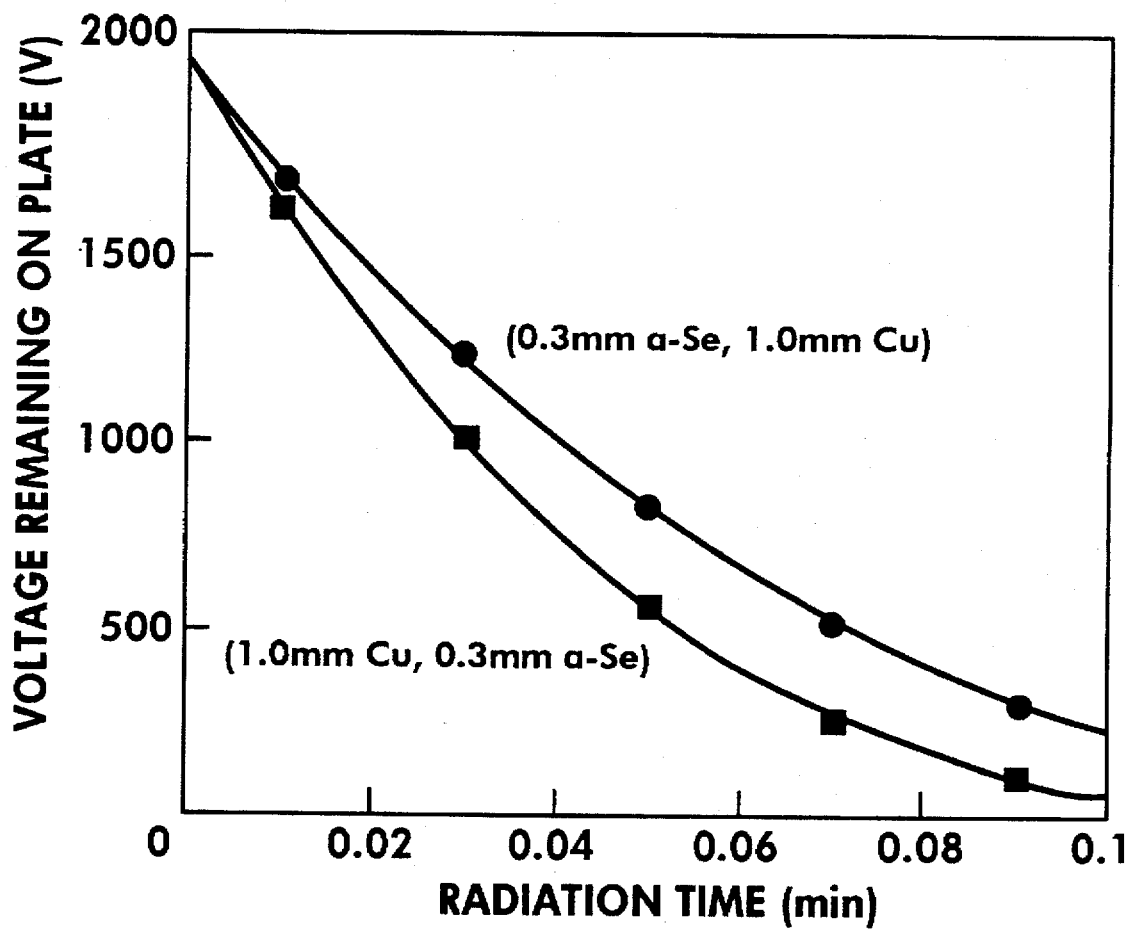
FIG. 4 illustrates radiative-discharge, or sensitivity curves obtained from a Co-60 therapy-machine with a detector composed of a 1 mm thick copper detector and an a-Se layer of 300 micron thickness; results show the detector facing towards and away from the x-ray source.

The image contrast and dynamic range of the imaging detector is highly dependent on the thickness of the photoreceptor material layer. With increased thickness in the photoreceptor material layer, the image contrast is increased while the dynamic range of the system is decreased, as illustrated in FIGS. 4 and 5. The thickness of the photoreceptor material layer deposited on the substrate is generally between 150 and 1000 microns, but may be greater if necessary, depending on the dynamic range required. FIG. 1 illustrates the detector components. More specifically, the detector 10 comprises a layer of a substrate 12, preferably a conductive substrate, onto which an insulating interface layer 14 of from 0.5 to 1.5 µm is deposited in a conventional manner. A layer of a photoreceptor material 16 is then deposited, also in conventional manner. An optional protective overcoat 18 may also be laid on the detector to prevent damage and to enhance image quality. Preferred material for the insulating interface layer include aluminum oxide, and preferred overcoat materials include cellulose acetate, parylene, polycarbonate and the like.

Figure 3:
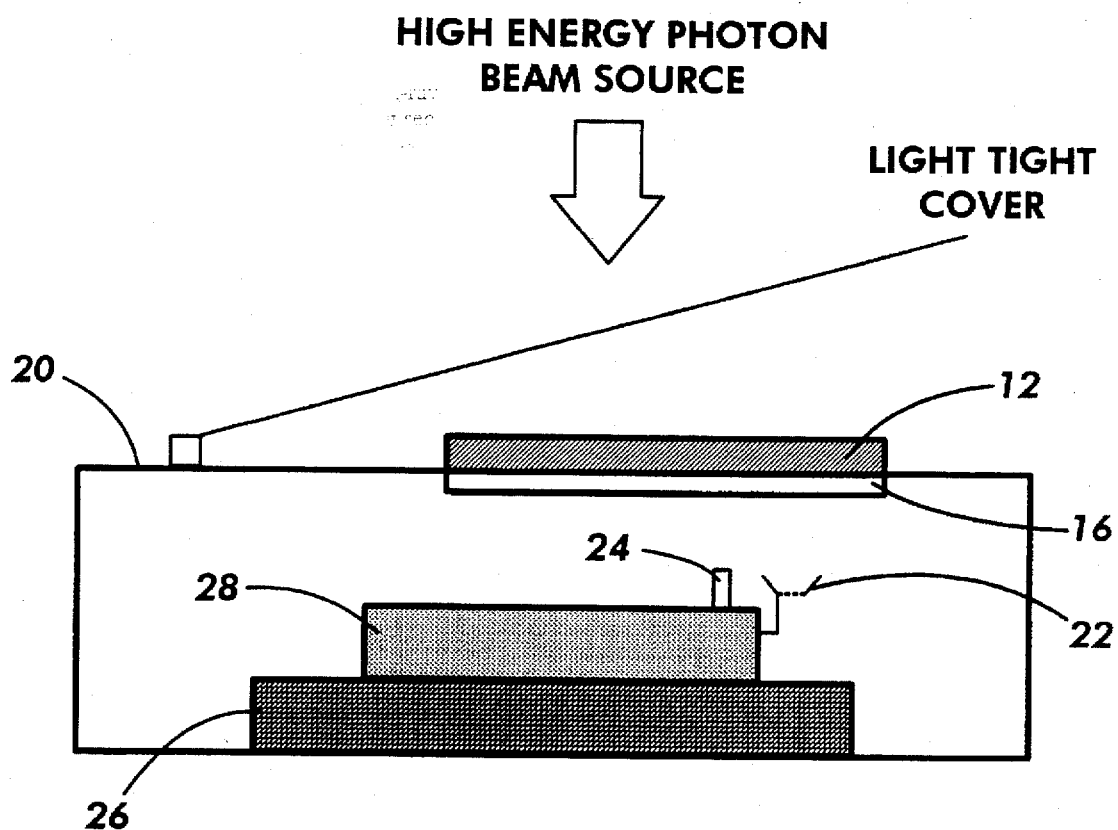
FIG. 3 illustrates the charging and reading assembly used.

FIG. 3 illustrates the charging and reading-detector system for data shown in the Figures. More specifically, detector 10 is enclosed in a light tight box 20 with the substrate layer 12 facing towards the source, the photoreceptor layer material 16 being on the opposite side. A biasing voltage may be applied to substrate layer 16 which converts photons to electrons, but if the x-ray photon converter is made of a non-conductive material, the biasing voltage is applied to a thin film of a conducting material, for example, ITO, aluminum etc. Before irradiation, a scorotron 22 is used to charge the photoreceptor layer 16 up to a given potential by ionizing the ambient air. The incoming x-ray beam thus interacts with the photon converter creating secondary electrons which deposit energy in the photoreceptor layer by electron-hole pair creation forming a latent image on the photoreceptor layer. An electrostatic probe 24 mounted on two independent x,y micropositioners 26 and 28 senses the remaining voltage distribution on the photoreceptor layer. The analog signal from this probe is then sent to an analog to digital converter (not shown) comprising an acquisition program. The two-dimensional image is then processed, analyzed and displayed in real time on a monitor.

The experimental evidence presented in the present application is the result of the imaging properties of an on-line a-Se based imaging system. This on-line imaging system is expected to present a solution to the problem of delays associated with portal films, and provides images of improved contrast and detected quantum efficiency. The phantom used for demonstrating the unexpected properties of the present method and detector is a 13 mm thick block of aluminum having a 25 cm$^2$ surface. The block contains 10 columns and 10 rows of holes of different depths and different diameters. For more details on the characteristics of the phantom, see *Med. Phys.* 1990, 17(5), 769(Table III).

Improvements in the quality of therapy images have been sought through the use of a detector whose (1) substrate is placed on the side of incidence of the photon x-ray source to remove patient scatter and thus improve the signal-to-noise ratio; and (2) substrate is made of a high density material, preferably a metal, to optimize the information-carrying quanta absorbed and spatial resolution.

In conventional xeroradiographic detector design, the substrate, generally aluminum, acts as a mere support and conductive base to the amorphous selenium detecting medium. The substrate's thickness and composition are of very little importance, if any. The detector serves its purpose well for diagnostic radiographs obtained with low energies, namely lower than 120 keV. However, at megavoltage energies, the detective quantum efficiency of the thin a-Se layer is very low, and there is an externally low transfer of information quanta from the patient onto the photoreceptor material surface. Furthermore, there is a large amount of scattered electrons from patients in megavoltage imaging which would be directly absorbed by the photoreceptor material layer resulting in highly blurred images.

The thickness and composition of the substrate of the present invention are important. The substrate is preferably conductive and has physical properties allowing it to absorb the largest number of x-rays impinging on it, while simultaneously offering low lateral scattering of electrons. The resolution can be improved by using a high physical density substrate like copper, iridium, brass, steel, iron, lead, tungsten and alloys thereof, or other alloys like stainless steel and the like, or materials like leaded glass or ITO on glass, since this will shorten the range of the electrons, thus shortening the lateral extent of the scattered electrons. For a given substrate thickness, a high physical density metallic substrate will absorb more photons than a metallic substrate of lower physical density. Further, a low atomic number is sought to reduce the angle of lateral electron scattering, but physical density increases as the atomic number increases. Thus, to obtain the optimal metal substrate for the therapy machine energy of concern, the effects of the physical density and the atomic number contributions to the image must be balanced. The problem of increasing the intensification factor at the photoreceptor stage of the detector while at the same time not reducing resolution of the image due to lateral scatter becomes a problem of optimization that must be dealt with in an independent manner for each substrate.

Comparisons between the different metals and the different positioning of the detector vis-a-vis the x-ray source were done with the Cobalt-60(Co-60) and a Clinical Linear Accelerator (Clinac-2300 C/D) radiotherapy machines, the latter being conventional devices in the art of radiation therapy. FIG. 5 shows that the sensitivity curves (voltage remaining on the detector versus the dose delivered) depend on the thickness of the a-Se layer. By varying parameters such as the initial voltage on the detectors or the thickness of the a-Se layer, a wide range of discharge curves can be generated. For instance, with a 150 microns a-Se layer, the curve is fairly linear for 0 to 20 cGy, with a nominal initial voltage of 2100 V. This can be compared with conventional therapy imaging film (RP Kodak therapy localization film) whose characteristic curve of optical density versus dose saturates at about 3 cGy (see FIG. 8).

The detector used with a higher physical density metallic substrate towards the source gives therapy images with higher contrast since the substrate shields the photoreceptor material from scattered radiation from the patient or subject. Furthermore, Monte Carlo simulation studies and preliminary physical measurements show that the proposed system also offers greater spatial resolution. The latter is due to the fact that the path length of electrons in the photoreceptor material is shorter than that of scattered photons.

A typical megavoltage detector or detector according to the present invention preferably comprises a high physical density metallic material as described above. The role of the high density material is to provide support to a thin multilayered structure used herein to detect and convert high energy x-ray photons and electrons to electrical charges to act as an intensifier of quanta and a filter of scattered radiation. The optimum thickness of the high physical density material is obtained when patient scattered electrons or photons are stopped and filtered while high spatial resolution is maintained. The thickness range is preferably between 0.2 and 5 mm. A thin layer of aluminum of a thickness of from 0.1 to 2 µm is then deposited on the high physical density substrate by conventional magnetron sputtering under reduced pressure. Also, a thin layer of aluminum oxide, referred to as a blocking layer, is formed or deposited on the aluminum electrode to reduce the charge injection from the aluminum metal electrode. The oxide layer is best obtained by oxidizing the aluminum electrode by plasma glow discharge in a reduced pressure and an oxygen enriched environment. The blocking layer could also be obtained by RF sputtering of aluminum oxide. The thickness of the blocking layer is preferably from 0.01 to 0.2 µm. A photoreceptor layer of amorphous selenium, preferably doped with arsenic and chlorine is then deposited by thermal evaporation under reduced pressure in a conventional manner. The level of doping of both arsenic and chlorine can be determined by anyone of ordinary skill in the art, and is selected to obtain good charge transport properties of the photoreceptor selenium layer as well as maintaining very low dark discharge current. The thickness of the amorphous selenium layer is preferably from 150 to 1000 μm, and most preferably 500 μm. A thin protective and passivating layer of cellulose acetate, polycarbonate or parylene having a thickness from 0.01 to 1 μm may then be deposited on the photoreceptor layer.

The detector may also comprise a self-scanning sensor consisting of a pixelized array of thin film transistors made of hydrogenated amorphous silicon or polycrystalline cadmium selenide with pixelized electrodes made of indium tin oxide (ITO). A photoreceptor amorphous selenium layer is then deposited directly on the pixelized ITO, and to minimize carrier injection, a blocking layer made of either a thin polymeric layer or a heavily doped alkaline selenium-arsenic alloy layer may be directly deposited on the main photoreceptor selenium layer. A thin metallic electrode made from conducting metal is deposited on top of the blocking layer. A high density material is then put in front of this arrangement. The high physical density material is in role, in nature and in thickness comparable to the detector described as the Example 1.

Another conceivable detector could comprise two groups of multi-strips conductors with one group being perpendicular to the other. A first group of multi-strip thin film conductors like aluminum is deposited on a low-density non-conducting substrate such as glass or plastic. A uniform thin blocking layer is then formed or deposited as described in Example 1. A photoreceptor selenium layer is also deposited as described in Example 1. A polymeric layer such as polycarbonate, polyester, polyimid and the like, and having on one side the second group of multi-strip conductors is then laminated on the photoreceptor selenium layer with the second group of multi-strip conductors being oriented perpendicularly to the first group. A high physical density intensifier is also used as described previously.

The present invention is based on the fact that the high density substrate is placed facing the x-ray source and the photoreceptor material is being discharged during the exposure of the patient. The charging and the reading process of the latent electrostatic image remaining on the photoreceptor material surface are similar to that used in conventional digital xeroradiography. Typically, a scanning non-contact electrostatic probe is used, but a multi-probe matrix, a photoinduced discharge scanning laser beam method, together with an active matrix self-active system, self-scan switching systems or projection system may also be employed. It should be noted that because of the geometry of the detector vis-a-vis the patient, the detector need not be inverted or taken out to a reading device. As shown in FIGS. 2-3, the detector is read from below directly in the imaging setup or device.

In the charging sequence, a scorotron is placed at a distance of 3-5 mm from the surface of the photoreceptor material layer. 6500 V are applied across the scorotron wires, while a voltage of 2100 V is applied across the grid. The grid is used to insure that the positive ions generated by the high voltage around the scorotron wires are deposited onto the photoreceptor material surface uniformly. The scorotron is moved by a mechanical stage several times over the whole surface of the detector. The detector is doubly charged to insure a uniform charge distribution. The surface can then be scanned at several key locations such as at the corners and at the center of the detector, to insure that the detector has a uniform exposure of about 2100 V. The conducting substrate, the grid and the scorotron must be referenced to the same potential (0 V or a biased voltage).

After charging, the detector is ready for megavoltage exposure. The detector should be oriented as shown in FIG. 2. During exposure, the electrons generated in the metal substrate and the photons that interact directly with the photoreceptor material will generate electron-hole pairs within the photoreceptor material layer. These pairs will then move under the influence of the electric field generated by the charging sequence. The negative charges will drift along the electric field lines and annihilate with the positive charges at the surface of the photoreceptor material layer. The positive charges will drift in the opposite direction towards the substrate and annihilate with the negative charges induced at this electrode. The latent image on the surface of the photoreceptor material will reflect the patient modulated x-ray beam intensity. The detector must once again be in the dark during the exposure sequence.

The latent electrostatic image must then be read out. There are several conventional methods available for this task. Electrostatic coupling probes can be used, placed in some array or alone. They sweep the surface several times depending on the number of probes in the array and the resolution of the scan desired. The scanning sequence can be carried out by either moving the probe array or by moving the detector assembly. Another method is to use lasers to scan the surface by inducing discharge on an area, or pixel, of the surface by shining the laser at the spot desired, and then sensing the discharge on the detector, at that region, with some capacitor coupled device. The whole detector would be scanned pixel by pixel in a raster manner. Whatever the reading sequence used, it must be done in the dark.

While the invention has been described in connection with specific embodiments thereof, it will be understood that it is capable of further modifications and this application is intended to cover any variations, uses or adaptations of the invention following, in general, the principles of the invention and including such departures from the present disclosure as come within known or customary practice within the art to which the invention pertains, and as may be applied to the essential features hereinbefore set forth, and as follows in the scope of the appended claims.

What is claimed is:

1. An imaging method for megavoltage imaging to monitor in real time the treatment beam field position vis-a-vis a target volume of a patient, comprising generating an image on a detector comprising a layer of a photoreceptor material deposited on a layer of a high density substrate by passing a photon beam first through the target volume of the patient and subsequently through the detector, the layer of high density substrate being on the side of incidence of the photon beam for intensifying photon quanta and filter scattered radiation from the patient induced by the photon beam, so that photons impinging on the high density substrate are converted to electrons, and an image is generated by the electrons subsequently traversing the photoreceptor material layer, whereby treated target volume of the patient is monitored on-line.

2. A method according to claim 1 wherein the high density substrate is copper, iridium, brass, lead, steel, iron, tungsten and alloys thereof, stainless steel, indium-tin-oxide on glass substrate or leaded glass.

3. A method according to claim 1 wherein the thickness of the layer of high density substrate is such that patient scattered electrons or photons are stopped and filtered while high spatial resolution is maintained.

4. A method according to claim 3 wherein the thickness of the layer of the substrate is from 0.2 to 5 mm, and the thickness of the layer of the photoreceptor material is from 50 to 1000 μm.

5. A method according to claim 1 wherein the photoreceptor material is amorphous selenium, mercuric iodide, cadmium telluride or lead oxide.

6. A method according to claim 5 wherein a layer of aluminum of a thickness of from 0.1 to 2 μm is deposited on the high density substrate and oxidized before depositing the photoreceptor thereon.

7. A method according to claim 5 wherein the photoreceptor material is amorphous selenium doped with arsenic and chlorine.

8. A method according to claim 1 wherein the photon beam is x-rays or gamma rays.

9. A method according to claim 1 wherein the electrostatic latent image formed on the photoreceptor is read by scanning with a non-contact probe or probe array, or a scanning laser beam.

10. An imaging method for megavoltage imaging to monitor, in real time, the treatment beam field position vis-a-vis a target volume of a patient, comprising generating an image on a detector comprising a first layer of amorphous selenium doped with arsenic and chlorine, the first layer being deposited on a second layer of copper, tungsten or alloys thereof, or stainless steel, by passing an x-ray beam first through the target volume of the patient and subsequently through the detector, the second layer being on the side of incidence of the photon beam for intensifying photon quanta and filter scattered radiation from the patient induced by the photon beam, so that photons impinging on the second layer are converted to electrons, and an image is generated by the electrons subsequently traversing the first layer, whereby the treated target volume is monitored on-line.

11. A detector for megavoltage imaging to monitor the treatment beam field position vis-a-vis the target volume of a patient, the detector comprising a layer of a high density substrate to intensify photon quanta and filter scattered radiation from the patient induced by a photon beam, and a layer of a photoreceptor material selected from the group consisting of amorphous selenium, mercuric iodide, cadmium telluride and lead oxide deposited thereon, wherein an image is generated by electrons traversing the photoreceptor material.

12. A detector according to claim 11 wherein the substrate is copper, iridium, brass, indium-tin-oxide on glass substrate, lead or tungsten.

13. A detector according to claim 11 wherein the thickness of the layer of high density substrate is such that patient scattered electrons or photons are stopped and filtered while high spatial resolution is maintained.

14. A detector according to claim 13 wherein the thickness of the layer of the substrate is from 0.2 and 5 mm, and the thickness of the layer of the photoreceptor material is from 50 to 1000 μm.

15. A detector according to claim 11 wherein a layer of aluminum of a thickness of from 0.1 to 2 μm is deposited on the high density substrate and oxidized before depositing the photoreceptor thereon.

16. A detector according to claim 11 wherein the photoreceptor material is amorphous selenium doped with arsenic and chlorine.

17. A detector for megavoltage imaging to monitor the treatment beam field position vis-a-vis the target volume of a patient, the detector comprising a layer of copper, tungsten or alloys thereof or stainless steel to intensify photon quanta and filter scattered radiation from a photon beam, and a layer of amorphous selenium deposited thereon wherein image is generated by electrons traversing on the amorphous selenium layer.

18. A detector according to claim 17, wherein the amorphous selenium is doped with arsenic and chlorine.

* * * * *